(12) United States Patent
Gerz et al.

(10) Patent No.: US 9,382,904 B2
(45) Date of Patent: Jul. 5, 2016

(54) DOSING PUMP UNIT

(75) Inventors: Sergei Gerz, Pfinztal (DE); Markus Simon, Dobel (DE)

(73) Assignee: Grundfos Management a/s, Bjerringbro (DK)

( * ) Notice: Subject to any disclaimer, the term of this patent is extended or adjusted under 35 U.S.C. 154(b) by 843 days.

(21) Appl. No.: 13/579,613

(22) PCT Filed: Feb. 16, 2011

(86) PCT No.: PCT/EP2011/000721
§ 371 (c)(1),
(2), (4) Date: Oct. 2, 2012

(87) PCT Pub. No.: WO2011/101118
PCT Pub. Date: Aug. 25, 2011

(65) Prior Publication Data
US 2013/0058796 A1 Mar. 7, 2013

(30) Foreign Application Priority Data
Feb. 18, 2010 (EP) .................................. 10001644

(51) Int. Cl.
| A61M 5/36 | (2006.01) |
| A61M 5/168 | (2006.01) |
| F04B 53/06 | (2006.01) |
| F04B 11/00 | (2006.01) |
| F04B 49/06 | (2006.01) |

(52) U.S. Cl.
CPC ............ *F04B 53/06* (2013.01); *A61M 5/16831* (2013.01); *A61M 5/16854* (2013.01); *A61M 5/365* (2013.01); *F04B 11/0041* (2013.01); *F04B 49/065* (2013.01); *F04B 2201/0202* (2013.01); *F04B 2203/0209* (2013.01)

(58) Field of Classification Search
CPC ............ A61M 5/365; A61M 5/16831; A61M 5/16854
USPC .............. 417/18, 44.1, 44.2, 412, 413.1, 415; 604/65, 67, 123, 151–153
See application file for complete search history.

(56) References Cited

U.S. PATENT DOCUMENTS

| 4,131,393 A | 12/1978 | Magnussen, Jr. |
| 4,396,385 A * | 8/1983 | Kelly et al. .................... 604/152 |
| 4,919,596 A * | 4/1990 | Slate et al. ...................... 417/18 |
| 2006/0145797 A1 | 7/2006 | Muramatsu et al. |

FOREIGN PATENT DOCUMENTS

| EP | 1 757 809 A1 | 2/2007 |
| JP | S55-125980 U | 9/1980 |

(Continued)

*Primary Examiner* — Peter J Bertheaud
(74) *Attorney, Agent, or Firm* — McGlew and Tuttle, P.C.

(57) ABSTRACT

A metering pump unit with a metering chamber (6), a positive-displacement body that adjoins the latter and can be moved by a positive-displacement drive (22), as well as a controller (30) for actuating the positive-displacement drive (22). The controller (30) is designed to actuate the positive-displacement drive (22) at least in a specific operating state in such a way that a stroke, in particular a pressure stroke, of the positive-displacement body is started at a first, lower stroke rate, and the stroke rate is increased to a second, elevated stroke rate as the pressure stroke (36) continues. A method is provided for controlling the positive-displacement drive (22) of such a metering pump unit.

21 Claims, 2 Drawing Sheets

(56) References Cited

FOREIGN PATENT DOCUMENTS

| | | |
|---|---|---|
| JP | H06-17762 A | 1/1994 |
| JP | H06-173860 A | 6/1994 |
| JP | H10-331762 A | 12/1998 |
| JP | 2000-136962 A | 5/2000 |
| JP | 2006-226239 A | 8/2006 |
| JP | 2008-178817 A | 8/2008 |
| JP | 2009-538640 A | 11/2009 |
| WO | 85/01993 A1 | 5/1985 |
| WO | 01/83989 A1 | 11/2001 |
| WO | 2006/108606 A1 | 10/2006 |
| WO | 2007/122621 A2 | 11/2007 |

\* cited by examiner

DOSING PUMP UNIT

CROSS REFERENCE TO RELATED APPLICATIONS

This application is a United States National Phase application of International Application PCT/EP2011/000721 and claims the benefit of priority under 35 U.S.C. §119 of European Patent Application EP 10001644.3 filed Feb. 18, 2010, the entire contents of which are incorporated herein by reference.

FIELD OF THE INVENTION

The invention relates to a metering pump unit with a metering chamber, a positive-displacement body that adjoins the metering chamber and can be moved by a positive-displacement drive, as well as a controller for actuating the positive-displacement drive as well as to a method for actuating a drive motor of such a metering pump aggregate.

BACKGROUND OF THE INVENTION

Metering pump aggregates (pump units) are known to be designed as positive-displacement pumps, which have a metering chamber with a positive-displacement body, for example in the form of a membrane. The problem when conveying degassing media is that gas bubbles can form in the metering chamber. This holds true in particular when the pump is shut down. These gas bubbles detract from metering accuracy, since the gas bubbles take up a portion of the volume of liquid to be metered, and are also compressible. In light of this fact, it is desirable to remove such gas bubbles from the metering chamber as quickly as possible. However, this cannot always be accomplished, and larger quantities of gas can accumulate in the metering chamber, in particular when the pump is shut down. At a certain air/liquid ratio, the pump can then be blocked, meaning that the metering pump can no longer aspirate any liquid.

SUMMARY OF THE INVENTION

An object of the invention is to provide an improved metering pump unit in which a failure caused by a larger accumulation of gas bubbles in the metering chamber can be prevented.

The metering pump unit according to the invention has a known metering chamber that adjoins or incorporates a positive-displacement body. The positive-displacement body can be moved by means of a positive-displacement drive, e.g., a drive motor. Also provided for actuating or regulating the positive-displacement drive is a controller, for example which sets or controls the velocity or speed of the positive-displacement drive. In addition, the metering pump unit is preferably provided with a detection system for detecting gas bubbles in the metering chamber. For example, such a system can have sensors arranged in the pump or metering head, and is known, for example, from WO 2006/108606A1.

According to the invention, the controller is designed in such a way as to actuate the positive-displacement drive in a special way in at least one operating state, e.g., if the detection system has detected gas bubbles in the metering chamber. For example, this special actuation can be selected by the controller at a specific volumetric share of gas bubbles in the stroke volume. However, this actuation could also be used at all times. To this end, the controller is designed or has a corresponding program to actuate the positive-displacement drive, in which a stroke, in particular a pressure stroke of the positive-displacement body, is started at a first, lower stroke rate, and the stroke rate is increased to a second, elevated stroke rate as the stroke or pressure stroke continues. For example, due to a higher stroke rate at the end of the stroke, which is achieved by a higher velocity of the positive-displacement drive, e.g., a higher speed of the drive motor, the pressure pulse generated as a result in the metering chamber causes the pressure valve, i.e., the check valve, to close late on the pressure side, so that liquid flows from the pressure line back into the metering head at the beginning of the next intake stroke. This improves the liquid/air ratio in the pressure chamber. In other words, the liquid percentage in the metering chamber is increased. In this way, a higher level of security is achieved against metering failure owing to an excessively high air percentage (airlocking). The elevated stroke rate further causes the gas bubbles to be expelled faster from the metering chamber, e.g., toward the end of the stroke.

Proceeding from the first, lower stroke rate, the velocity can also be increased in several stages to a second, possibly a third or more, elevated stroke rates. The velocity increase can here be sudden, or also happen in the form of a ramp.

Even if the controller is designed to select the special actuation or actuation characteristics described above and below for a pressure stroke, it must be understood that this described special actuation can also be used in the intake stroke, i.e., the stroke rate can be increased toward the end of the intake stroke, for example.

In addition, this special actuation can be automatically initiated in response to the controller detecting gas bubbles, or a manually activation option can be provided. Further, the controller could also always execute such an actuation during the operation of the metering pump unit.

The controller is preferably designed to actuate the positive-displacement drive pursuant to the special drive strategy, e.g., after detecting gas bubbles in the metering chamber, in such a way as to increase the stroke rate toward the end of the stroke or pressure stroke. This means that the majority of the stroke takes place at one or several lower stroke rates, and the mentioned higher pressure rate only comes into operation in a comparably small end region of the stroke, so that no volumetric flow higher than the setpoint volumetric flow is conveyed.

In another preferred embodiment, the controller is designed to actuate the positive-displacement drive, e.g., after detecting gas bubbles in the metering chamber, in such a way that an intake stroke following the pressure stroke starts out at an elevated, preferably the second stroke rate. This yet again facilitates the flow back from the pressure channel.

It is preferred that the portion of the stroke with the second, elevated stroke rate, meaning preferably the last portion of the stroke, comprise between 2 and 15% of the entire stroke. The overall conveyed flow over the entire stroke, in particular the pressure stroke, only increases slightly as the result of the faster stroke rate or drive speed of the drive motor toward the end of the stroke. It must here be understood that the stroke involving a percentage of between 2 and 15% at the elevated stroke rate does not have to be the maximum possible stroke of the metering pump unit. Rather, it can be a reduced stroke, from which a portion in turn takes place at the elevated stroke rate.

It is further preferred that the controller be designed to set the first, lower stroke rate during the control operation in response to the detection of gas bubbles in such a way that a desired setpoint conveyed flow of the liquid to be conveyed can be achieved via the stroke of the positive-displacement body, taking into account the volume of the gas bubbles. This means that the overall drive takes place for a higher conveyed volume, so as to balance out the volume and compressibility of the gas bubbles, and ensure that essentially the desired setpoint conveyed flow of the liquid to be conveyed can be reached.

In another preferred embodiment, the first stroke rate is optimized in such a way that gas bubbles in the metering chamber have enough time remaining to rise in the pressure channel in the metering chamber, so that the gas bubbles are expelled or removed from the metering chamber as completely as possible. For this purpose, the stroke rate should not be set too high. This can also be taken into account in a corresponding control program of the controller for use in detecting gas bubbles or a quantity of gas bubbles over a preset limit.

The first, lower stroke rate is preferably less than or equal to one hundred strokes per minute, wherein the velocity can also be less than twenty strokes per minute, for example, when conveying creep quantities. The second, elevated stroke rate preferably lies between one hundred twenty and three hundred strokes per minute.

It is further preferred that the controller be designed to set the first lower stroke rate, the second elevated stroke rate, and the percentage of the partial stroke at the second stroke rate in the entire stroke, in particular pressure stroke, in such a way that an average conveyed flow corresponding to the setpoint conveyed flow can be achieved over the entire stroke. This means that the elevated stroke rate in the second portion or at the end of the stroke with an associated elevated conveyed flow is balanced out by a correspondingly lower conveyed flow owing to a lower stroke rate or drive speed in the first portion of the stroke. In addition, reducing the drive speed or stroke rate in the first portion of the pressure stroke facilitates the removal of the gas bubbles from the metering chamber, as described above.

The detection system for detecting gas bubbles in the metering chamber preferably has at least one pressure sensor for acquiring the pressure of the liquid conveyed by the metering pump, and is designed in such a way as to detect the presence of gas bubbles based on the pressure values acquired by the at least one pressure sensor. The pressure values can be compared with setpoint values for this purpose. The velocity of the positive-displacement drive set by the controller can here simultaneously be used to select the corresponding setpoint pressure values, for example from a memory in the detection system. The detection system can be designed as a self-contained electronic unit, but also form an integrated electronic arrangement with the controller. In particular, the detection system can be realized as software in a controller, aside from the required hardware, such as sensors.

It is further preferred that the at least one pressure sensor be arranged in or on the metering chamber or a pressure channel extending downstream away from the metering chamber. This means that the sensor is preferably situated as closely as possible to the metering chamber, so that it can acquire the delivery pressure of the pump in an adjoining hydraulic system, undistorted by outside influences. In addition, it becomes possible to integrate the sensor into the metering pump unit, and in particular a pump head of the metering pump unit, making it unnecessary to incorporate an external sensor while mounting the metering pump unit, and connect it with the metering pump unit or controller or detection system for signal transmission. The required systems or lines for signal transmission can in this way also be integrated into the metering pump unit in a protected manner.

In another preferred embodiment, the detection system is designed in such a way as to acquire the pressure progression over at least one pressure stroke of the positive-displacement body, and detect the presence of gas bubbles based upon the pressure progression. The pressure progression can here also preferably be compared with a prescribed setpoint progression. In case that gas bubbles are present in the metering chamber, the pressure generally only starts to rise after a certain delay at the beginning of the pressure stroke given the compressibility of the gas. For example, the detection system can detect gas bubbles by determining whether the pressure progression rises immediately after the pressure stroke begins, or after a certain delay. If this delay exceeds a preset limit, it may be concluded on that basis that a certain quantity of gas is present in the metering chamber. In addition, it also becomes possible to infer the quantity of gas in the metering chamber from the delay or pressure progression.

For this reason, the detection system is preferably designed to determine the percentage of gas bubbles in the entire stroke volume. The special drive or traversing program described above can be selected for actuating the positive-displacement drive if the controller has detected gas bubbles once a certain limit for the percentage of gas bubbles in the overall volume of the metering chamber has been detected. The limit is preferably selected in such a way as to reliably prevent a failure of conveying operations at below the limit, and do so as well after the limit has been reached as the result of the special drive strategy, which is then selected by the controller.

As a consequence, once the controller has detected gas bubbles with a percentage of the stroke volume that exceeds a preset first limit, it is preferably designed to actuate the positive-displacement drive in such a way that a stroke, in particular pressure stroke, of the positive-displacement body is initiated at a first, lower stroke rate, and increase the stroke rate to a second, elevated stroke rate as the stroke continues. The limit is selected in such a way that the controller executes the usual program for controlling the drive given lower percentages of gas in the volume of the metering chamber, and not the special program described above or the special drive strategy described above. The limit here reflects a gas percentage of the stroke volume low enough to prevent a conveying failure on the part of the pump. The limit is selected in such a way that the special drive strategy described above, in which the stroke rate is elevated toward the end of the stroke, is chosen starting at a gas percentage where a conveying failure becomes a concern.

It is preferred that the first limit correspond to a volume percentage >65%, preferably a volume percentage of 70 or 75%, of the stroke volume. This means that, when the gas volume makes up less than 65%, 70% or 75% of the stroke volume, the special drive strategy is not selected yet, and the stroke rate or drive velocity of the positive-displacement drive is increased in particular in the pressure stroke toward the end of the stroke only when such a high gas percentage is detected.

It is further preferred that the controller be designed to actuate the positive-displacement drive in such a way that the strokes, in particular pressure strokes, of the positive-displacement body begin at a lower stroke rate, and the stroke rate increases to a second, elevated stroke rate as the stroke continues, until the detection system detects that the percentage of gas bubbles in the stroke volume is lower than a preset second limit. This ensures that the metering pump will be operated in the mode with the elevated stroke rate toward the end of a stroke until such time as a level of operational security is ensured that eliminates the concern of a conveying or metering failure. The preset second limit is preferably smaller than the first limit, in order to avoid repeated oscillation between the two operating modes.

In an especially preferred embodiment, the positive-displacement drive is a drive motor, in particular a stepping motor. Such a stepping motor can be used to very precisely control the strokes of the positive-displacement body, since the drive motor is rotated in a plurality of individual steps. The number of individual steps per unit of time can be used to vary the speed, and hence the stroke rate. In addition, the stroke length can also be precisely defined by turning the drive motor by a specific number of steps. However, use can also be made of other rotating drive motors, for example EC motors or servomotors. Rotating drive motors are provided with a gearing that converts the rotational motion into a linear motion, for example a cam, a cam drive, a crank drive or a worm drive. An electrical linear drive or linear motor can also be used in place of a rotating drive motor, however.

The invention further relates to a method for controlling a positive-displacement drive of a metering pump unit. Preferably involved here is a metering pump unit according to the preceding specification. In particular when gas bubbles are detected in the metering chamber, preferably when a specific percentage of gas bubbles are detected in the entire stroke volume, the method is designed to actuate a positive-displacement drive for moving a positive-displacement body of the metering pump in such a way that a stroke, in particular a pressure stroke, of the positive-displacement body is begun at a first, low stroke rate, after which the stroke rate is increased to a second, elevated stroke rate as the stroke continues. This increase is preferably effected toward the end of the stroke or pressure stroke, so that the majority of the stroke takes place at a first, lower stroke rate. The first, lower stroke rate can be increased to the second, elevated stroke rate suddenly, or ascend continuously or in several steps. The controller described above can be designed accordingly for this purpose. Otherwise, the method is preferably implemented as described above based on the metering pump unit.

The invention will be described by example below based on the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
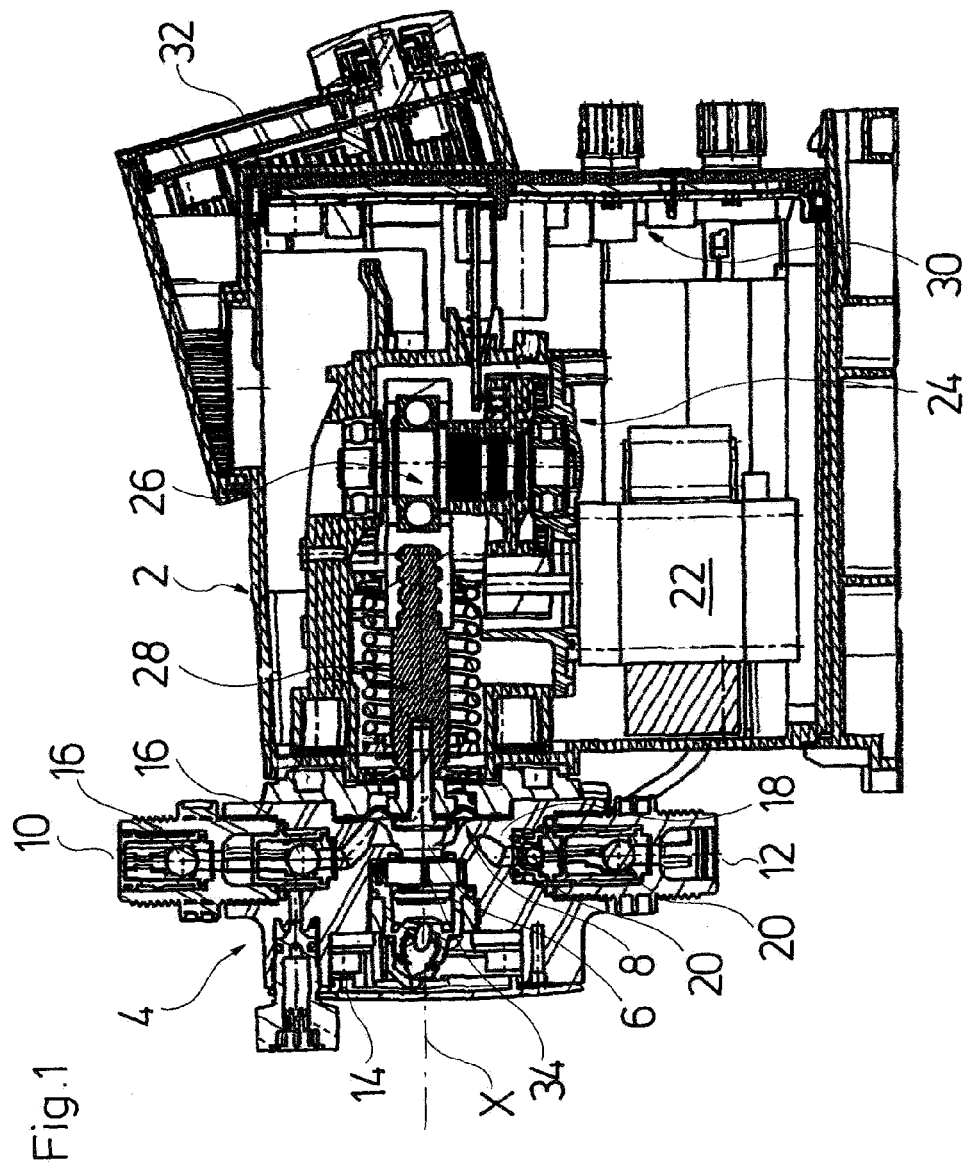
FIG. 1 is a side view through a metering pump unit according to the invention.

Referring to the drawings in particular, the depicted pump unit has a drive casing 2, the front of which has secured to it a pump head 4. The pump head 4 incorporates a metering chamber 6, which is bordered on one side by a membrane 8. The membrane 8 is linearly movable along the stroke axis X. The metering chamber 6 is connected with a pressure port 10 and a suction port 12. The pressure channel 14 joins the metering chamber 6 with the pressure port 10, and incorporates two check valves 16. Two check valves 20 are situated in the intake channel 18, which joins the metering chamber 6 with the intake port 12.

Situated inside the drive casing 2 is a positive-displacement drive in the form of an electric drive motor 22, preferably in the form of a stepping motor. The drive motor 22 uses a gearing 24 and a cam 26 to drive a connecting rod 28, which imparts a linear stroke motion to the membrane 8 along the stroke axis X. A controller or electronic control system 30 is arranged in the drive casing 2 to control the drive motor 22. The electronic control system 30 controls the drive motor 22 with respect to speed and rotational angle as a function of prescribed parameters. These can be set using an operating unit 32, for example. In addition, the electronic control system 30 has a detection system for detecting gas bubbles in the metering chamber 6. This detection system can be realized as hardware and/or software in the electronic control system 30. The detection system contains a pressure sensor 34, which determines the pressure in the metering chamber 6, and relays corresponding output signals to the electronic control system 36 by way of a connecting line not shown here.

Based on the pressure progression in the pressure stroke, the pressure sensor 34 is able to detect whether gas bubbles are present in the metering chamber. In this case if gas bubbles are present in the metering chamber 6, the pressure at the beginning of the pressure stroke rises after a delay, since the gas in the gas bubbles is initially compressed. The duration of this delay is representative for the percentage of gas volume in the stroke volume, so that the electronic control system 30 or the detection system realized therein can also determine the percentage quantity of the gas in the stroke volume.

If a predetermined portion of gas is determined by this detection system, for example a gas portion exceeding 70% of the stroke volume, there is a danger that conveying or metering will fail, meaning that the metering pump would not aspirate any more liquid to be conveyed during the intake stroke, and the stroke of the membrane 8 would instead only compress and expand the gas volume. In order to prevent this, the electronic control system initiates a specific control process or specific control strategy for controlling the drive motor 22 at a prescribed portion of gas, e.g., measuring 70%.

Figure 2:
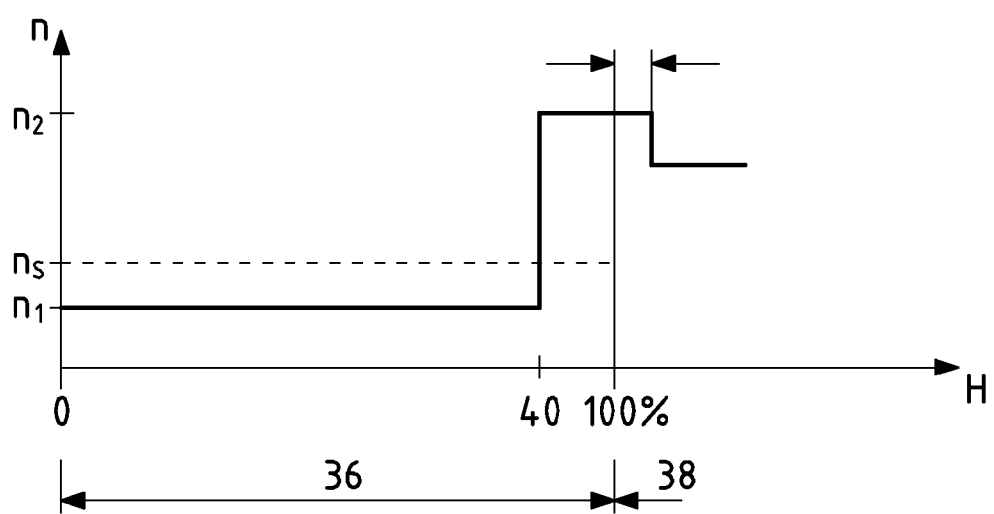
FIG. 2 is a diagram showing the speed of the drive motor as a function of a pressure stroke.

This control strategy implies that the drive motor 22 is initially operated at a lower speed n1 at the start of the pressure stroke in this example, as depicted on FIG. 2. The speed of the drive motor 22 is proportional to the stroke rate of the membrane 8. The motor speed n is shown as a function of the stroke H on FIG. 2 Shown in detail here is a pressure stroke 36, and next to that an intake stroke 38, which is no longer shown completely. The pressure stroke 36 is started at a lowered speed n1 of the drive motor 22, so that the membrane 8 correspondingly initially traverses at a lower stroke rate. At the end of the pressure stroke 36, the speed is increased from the lower speed n1 to an elevated speed n2 from point 40. This also increases the stroke rate to a proportionally elevated stroke rate. The last portion of the pressure stroke 36, for example the last 2 to 20% of the pressure stroke, takes place at this elevated speed n2. The beginning of the intake stroke 38 also takes place at this elevated speed n2, after which the speed in the intake stroke can again be reduced. As a result of the elevated speed n2 and elevated stroke rate associated therewith at the end of the pressure stroke 36, an elevated pressure pulse is generated at the end of the pressure stroke in the metering chamber 6, which then delays closure of the check valve 16 at the beginning of the suction stroke 38. In this way, fluid flows back from the part of the pressure channel 14 lying downstream from the first check valve 16, i.e., the one facing the metering chamber 6, at the beginning of the intake stroke. This increases the percentage of liquid in the metering chamber 6, and a gas-liquid ratio in the metering chamber is correspondingly reduced, thereby increasing the operational safety with respect to a conveying failure, since the percentage of gas in the overall volume is diminished accordingly.

The low speed n1 and elevated speed n2, along with the portion of the pressure stroke between point 40 and the end of the pressure stroke 36 that takes place at the elevated drive speed n2, are selected in such a way that a setpoint conveyed flow can be achieved on average for the overall pressure stroke that normally would not be reached at a setpoint speed ns. In this case, ns is the setpoint speed at which the drive motor 22 would be operated under normal conditions to reach a setpoint conveyed flow. Accordingly, when implementing the described drive strategy for ensuring the conveying process, the selected lower speed n1 is less than the setpoint speed ns, and the selected elevated speed n2 is higher than the setpoint speed ns, thereby yielding a setpoint speed ns and setpoint conveyed flow associated therewith on average over the overall pressure stroke 36. Another advantage to the reduction in speed at the beginning of the pressure stroke and lower stroke rate associated therewith is that gas bubbles in the metering chamber 6 have more time to rise in the metering chamber in the pressure channel 14 at a lower stroke rate, so that gas bubbles can also be more efficiently conveyed out of the metering chamber.

The electronic control system 30 continues the drive strategy described based on FIG. 2 until the detection system uses the pressure sensor 34 to detect a gas portion in the volume of the metering space 6 lying below a preset limit. This limit is preferably lower than the limit at which the described drive strategy is begun. In other words, this drive strategy is potentially carried out in this way for several pressure strokes 36.

While specific embodiments of the invention have been shown and described in detail to illustrate the application of the principles of the invention, it will be understood that the invention may be embodied otherwise without departing from such principles.

The invention claimed is:

1. A metering pump unit comprising:
   a metering chamber;
   a positive displacement drive;
   a positive-displacement body that adjoins the metering chamber and can be moved by the positive-displacement drive; and
   a controller for actuating the positive-displacement drive, the controller actuating the positive-displacement drive at least in a specific operating state in such a way that a pressure stroke of the positive-displacement body is started at a first, lower stroke rate, and the stroke rate is increased to a second, elevated stroke rate as the pressure stroke continues, the controller being provided with a detection system for detecting gas bubbles in the metering chamber, wherein the controller actuates the positive-displacement drive in such a way after detecting gas bubbles in the metering chamber that the pressure stroke of the positive-displacement body is started at a first, lower stroke rate, and the stroke rate is increased to a second, elevated stroke rate as the pressure stroke continues.

2. The metering pump unit according to claim 1, wherein the controller actuates the positive-displacement drive in such a way that the stroke rate is increased toward the end of the pressure stroke.

3. The metering pump unit according to claim 1, wherein the controller actuates the positive-displacement drive in such a way that an intake stroke following the pressure stroke is started at an elevated stroke rate.

4. The metering pump unit according to claim 1, wherein the portion of the pressure stroke at the second elevated stroke rate comprises between 2 and 15% of the entire stroke.

5. The metering pump unit according to claim 1, wherein:
   the controller is provided with a detection system for detecting gas bubbles in the metering chamber to determine a volume of the gas bubbles;
   the controller is designed to set the first, lower stroke rate in such a way that a desired setpoint conveyed flow of the liquid to be conveyed can be achieved via the pressure stroke of the positive-displacement body, taking into account the volume of the gas bubbles.

6. The metering pump unit according to claim 1, wherein the controller is designed to set the first, lower stroke rate, the second, elevated stroke rate, and the percentage of a partial stroke at the second stroke rate in an overall pressure stroke in such a way that an average conveyed flow corresponding to the setpoint conveyed flow can be achieved over the entire stroke.

7. The metering pump unit according to claim 1, wherein the detection system has at least one pressure sensor for acquiring the pressure of the liquid conveyed by the metering pump, and is designed to detect the presence of gas bubbles based on the pressure values acquired by the at least one pressure sensor.

8. The metering pump unit according to claim 7, wherein the at least one pressure sensor is arranged in or on the metering chamber or a pressure channel extending downstream from the metering chamber.

9. The metering pump unit according to claim 7, wherein the detection system is designed to acquire a pressure progression over at least one pressure stroke of the positive-displacement body, and detect the presence of gas bubbles based on the pressure progression.

10. The metering pump unit according to claim 1, wherein the detection system is designed to determine the portion of gas bubbles in the overall volume of the metering chamber.

11. The metering pump unit according to claim 10, wherein the controller actuates the positive-displacement drive after detecting gas bubbles comprising a percentage of the volume of the metering chamber that exceeds a preset first limit in such a way that the pressure stroke of the positive-displacement body is started at a first, lower stroke rate, and the stroke rate is increased to a second, elevated stroke rate as the stroke continues.

12. The metering pump unit according to claim 11, wherein the first limit corresponds to a volumetric percentage that exceeds 65% of the stroke volume.

13. The metering pump unit according to claim 1, wherein the controller is designed to actuate the positive-displacement drive to cause the strokes of the positive-displacement body to start at a first, lower stroke rate, and the stroke rate is increased to a second, elevated stroke rate as the pressure stroke continues, until the detection system detects that the percentage of gas bubbles in the volume of the metering chamber is less than a preset second limit.

14. The metering pump unit according to claim 1, wherein the positive-displacement drive comprises a stepping motor.

15. A method for actuating a positive-displacement drive of a metering pump unit, the method comprising the steps of:
   providing the metering pump comprising a metering chamber, the positive displacement drive, a positive-displacement body that adjoins the metering chamber and can be moved by the positive-displacement drive and a controller;
   actuating the positive-displacement drive for moving the positive-displacement body in such a way that a pressure stroke, of the positive-displacement body is started at a first, lower stroke rate, and the stroke rate is increased to a second, elevated stroke rate as the pressure stroke continues;

providing a detection system for detecting gas bubbles in the metering chamber wherein the step of actuating the positive-displacement drive, with the controller, occurs after detecting gas bubbles in the metering chamber.

16. The method according to claim 15, wherein the detection system is designed to determine the portion of gas bubbles in the overall volume of the metering chamber.

17. The method according to claim 16, wherein the controller actuates the positive-displacement drive after detecting gas bubbles comprising a percentage of the volume of the metering chamber that exceeds a preset first limit in such a way that a pressure stroke of the positive-displacement body is started at a first, lower stroke rate, and the stroke rate is increased to a second, elevated stroke rate as the pressure stroke continues.

18. A metering pump unit comprising:
a metering chamber;
a positive-displacement body movable relative to said metering chamber in a pressure stroke to move fluid out of said metering chamber;
a positive displacement drive moving said positive-displacement body in said pressure stroke;
a controller actuating said positive-displacement drive to start said pressure stroke at a first lower stroke rate, and then increase a stroke rate to a second elevated stroke rate as said pressure stroke progresses;
a detection system for detecting gas bubbles in said metering chamber;
said controller changing operation of said positive-displacement drive when said detection system detects gas bubbles in the metering chamber.

19. A metering pump unit in accordance with claim 18, wherein:
said controller actuates said positive-displacement drive to start said pressure stroke at said first lower stroke rate, and then increase said stroke rate to said second elevated stroke rate as said pressure stroke progresses, when said detection system detects gas bubbles in said metering chamber.

20. The metering pump unit according to claim 18, wherein;
said positive-displacement body is movable relative to said metering chamber in an intake stroke to move fluid into said metering chamber;
said positive displacement drive moves said positive-displacement body in said intake stroke;
said controller actuates said positive-displacement drive to start said intake stroke at an elevated intake stroke rate and then decline to a lower intake stroke rate as said intake stroke progresses.

21. A metering pump unit in accordance with claim 20, wherein:
said controller actuating said positive-displacement drive to perform a plurality of said pressure strokes, one of said pressure strokes starting at said first lower stroke rate, and increasing to said second elevated stroke rate as said one pressure stroke progresses, when said detection system detects gas bubbles in the metering chamber;
said controller actuating said positive-displacement drive to perform a plurality of said intake strokes, one of said intake strokes starting at an elevated intake stroke rate and declining to a lower intake stroke rate as said one intake stroke progresses, said one intake stroke occurring directly after said one pressure stroke.

* * * * *